United States Patent [19]

Ibe et al.

[11] Patent Number: 5,187,729
[45] Date of Patent: Feb. 16, 1993

[54] METHOD AND APPARATUS FOR DETECTING A CRYSTALLOGRAPHIC AXIS OF A SINGLE CRYSTAL INGOT FOR "OF" DETERMINATION

[75] Inventors: Hiroyaki Ibe, Fukui; Seiichi Terashima; Tsumoru Masui, both of Gunma, all of Japan

[73] Assignee: Shin-Etsu Handotai Co., Ltd., Tokyo, Japan

[21] Appl. No.: 838,046

[22] Filed: Feb. 19, 1992

[30] Foreign Application Priority Data

Feb. 19, 1991 [JP] Japan .................................. 3-45458

[51] Int. Cl.⁵ ......................................... G01N 23/207
[52] U.S. Cl. ......................................... 378/73; 356/31
[58] Field of Search ............................ 378/73; 356/31

[56] References Cited

U.S. PATENT DOCUMENTS 4,884,887 12/1989 Vanderwater ...................... 356/31

Primary Examiner—Constantine Hannaher
Assistant Examiner—Don Wong
Attorney, Agent, or Firm—Whitham & Marhoefer

[57] ABSTRACT

A method and an apparatus for detecting a crystallographic axis of a single crystal ingot based on the X-ray diffractometry, wherein and whereby a crystal habit line of the single crystal ingot is optically detected first, and thereafter making use of the geographical relation of the crystallographic axis to the crystal habit line, the crystallographic axis is detected with improved economy of time and labor and with improved precision, so that the orientation flat (OF) is made in the right place and direction.

2 Claims, 6 Drawing Sheets

METHOD AND APPARATUS FOR DETECTING A CRYSTALLOGRAPHIC AXIS OF A SINGLE CRYSTAL INGOT FOR "OF" DETERMINATION

BACKGROUND OF THE INVENTION

The present invention relates to a method and an apparatus for inspecting a single crystal ingot by means of the X-ray diffractometry to detect the direction of a crystallographic axis so as to determine the direction for an orientation flat (hereinafter merely referred to as "OF") to be made in the side of the single crystal ingot.

A semiconductor wafer to be made into substrates for semiconductor electronic devices is brought into being in the following manner: a single crystal ingot of a semiconductor material such as silicon is produced by means of a single crystal growing method such as the Czochralski (CZ) method; the ingot is then machined into a cylindrical form, and it is sliced into thin plates by cutting it in a direction substantially normal to the axis of the cylinder; next, the thin plates are lapped, etched and polished and eventually they become thin round disks having a mirror face on one side of them. Now, the thus made semiconductor wafers would be completely circular and have no visual clue to indicate any crystallographic orientation. For this reason, before being sliced into thin disks, the single crystal ingot is machined to have an orientation flat, which is a flat surface made in the side of the single crystal ingot in a manner such that the flat is normal to a crystallographic axis; the OF thus formed facilitates stage positioning of the resulting wafers, e.g., at the stage where optical pattern is given. Also, in some cases more than one orientation flat is made in a single crystal cylinder.

Naturally, a high precision is required in determining the direction of the OF to be made, and conventionally the crystallographic axes have been detected by means of the X-ray diffractometry (ref. Japanese Patent Application Kokoku No. 62-116243, for example).

PROBLEMS THE INVENTION SEEKS TO SOLVE

However, even in this sophisticated detective method based on the X-ray diffractometry, the procedure is not simple: the X-rays are irradiated to a spot in the surface of the single crystal cylinder (measurement point) while the cylinder is rotated about its axis of rotation at a constant angular speed and the scattered X-ray radiation is inspected from different angles by an X-ray detector to determine whether or not a crystallographic axis is being X-rayed. Thus, it is necessary to conduct the measurement for a large number of times from different directions, and as the result, the procedure takes time and labor, and consequently the method, as it is, is not very rational; more importantly, since the measurement is conducted for quite a few times, the accumulated error becomes substantial, and the accuracy of the result in determining the crystallographic axis wants further improvement.

It is conceivable to install a plurality of X-ray detectors to measure the X-ray scattering from different angles at a time; however, this will complicate the apparatus and push up the apparatus cost.

The present invention was contrived in view of the above problem, and, therefore, it is an object of the invention to provide an improved method and apparatus which simplifies and rationalizes the otherwise complicated and time-consuming operation of detecting the direction of the crystallographic axis, which will determine the direction for an OF with a high precision and efficiency.

MEANS TO SOLVE THE PROBLEMS

In order to attain the objects of the invention, a method is proposed for detecting a crystallographic axis of a single crystal ingot based on the X-ray diffractometry, which comprises: turning the single crystal ingot slowly about its center line (axis of rotation); optically detecting a crystal habit line; stopping the single crystal ingot from turning when a crystal habit line is detected; determining the rotational direction which will bring a crystallographic axis into the measurement point of the X-ray system sooner; turning the single crystal ingot in the thus determined direction at a much slower speed; detecting the crystallographic axis by means of the X-ray system.

Also, the present invention proposes an apparatus for detecting a crystallographic axis of a single crystal ingot based on the X-ray diffractometry comprising: a turn means capable of holding and turning the single crystal ingot about the center line (axis of rotation) thereof at a low speed and at a much lower speed selectively, and stopping at an arbitrary angular position; a crystal habit line detector means for optically detecting a crystal habit line of the single crystal ingot; and an X-ray system for detecting a crystallographic axis of the single crystal ingot making use of X-ray diffraction.

EFFECTS

Thus, according to the invention, a crystal habit line of the single crystal ingot is optically detected promptly by the crystal habit line detector means, and since the crystallographic axes hold a fixed geometrical relation with the crystal habit lines, it is now possible to find out the approximate location of the crystallographic axes; thus, by turning the ingot in the direction which will bring one of the crystallographic axes into the measurement point of the X-ray system sooner, it is possible to shorten the time until the crystallographic axis is detected. Once the aimed crystallographic axis is known to be in the vicinity, that is, when the crystal habit line is found, the rotational speed of the turn means is reduced and the measurement is conducted very carefully. Then, the crystallographic axis is accurately and promptly detected by means of the X-ray system, so that the measurement operation becomes less time-consuming and more accurate, and as the result, the OF can be made with high precision.

Also, according to the invention, the crystal orientation detecting apparatus is only additionally provided with a comparatively inexpensive crystal habit line detector means attached to the existing X-ray system, so that the apparatus remains as a relatively simple and inexpensive apparatus.

BRIEF DESCRIPTION OF DRAWINGS

FIGS. 5a and 5b are schematic drawings to show a geometrical relationship between a crystal habit line and the OF;

EMBODIMENT

Next, an embodiment of the invention will be explained with reference to the attached drawings.

Figure 1:
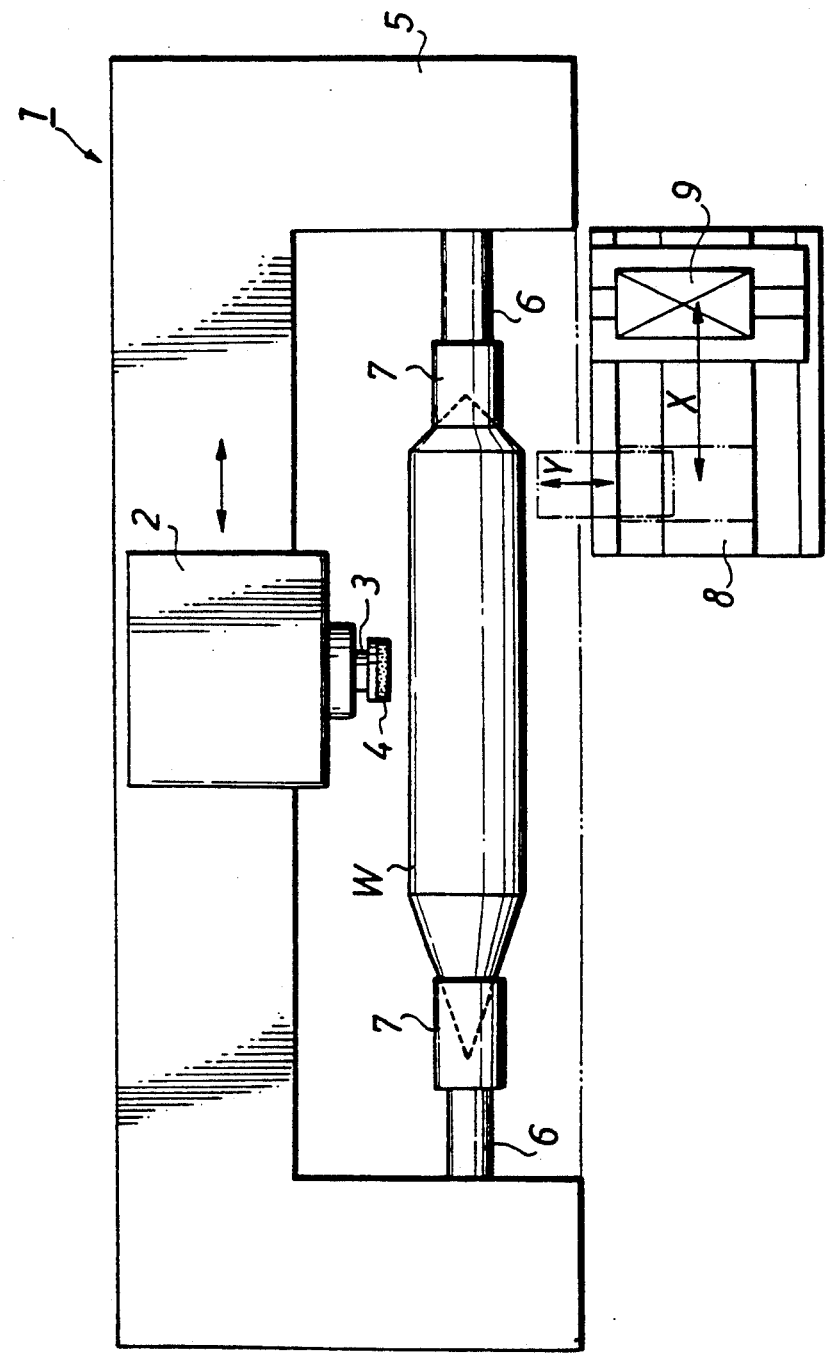
FIG. 1 is a top plan view of an embodiment of the crystal orientation detecting apparatus according to the invention.
Figure 2:
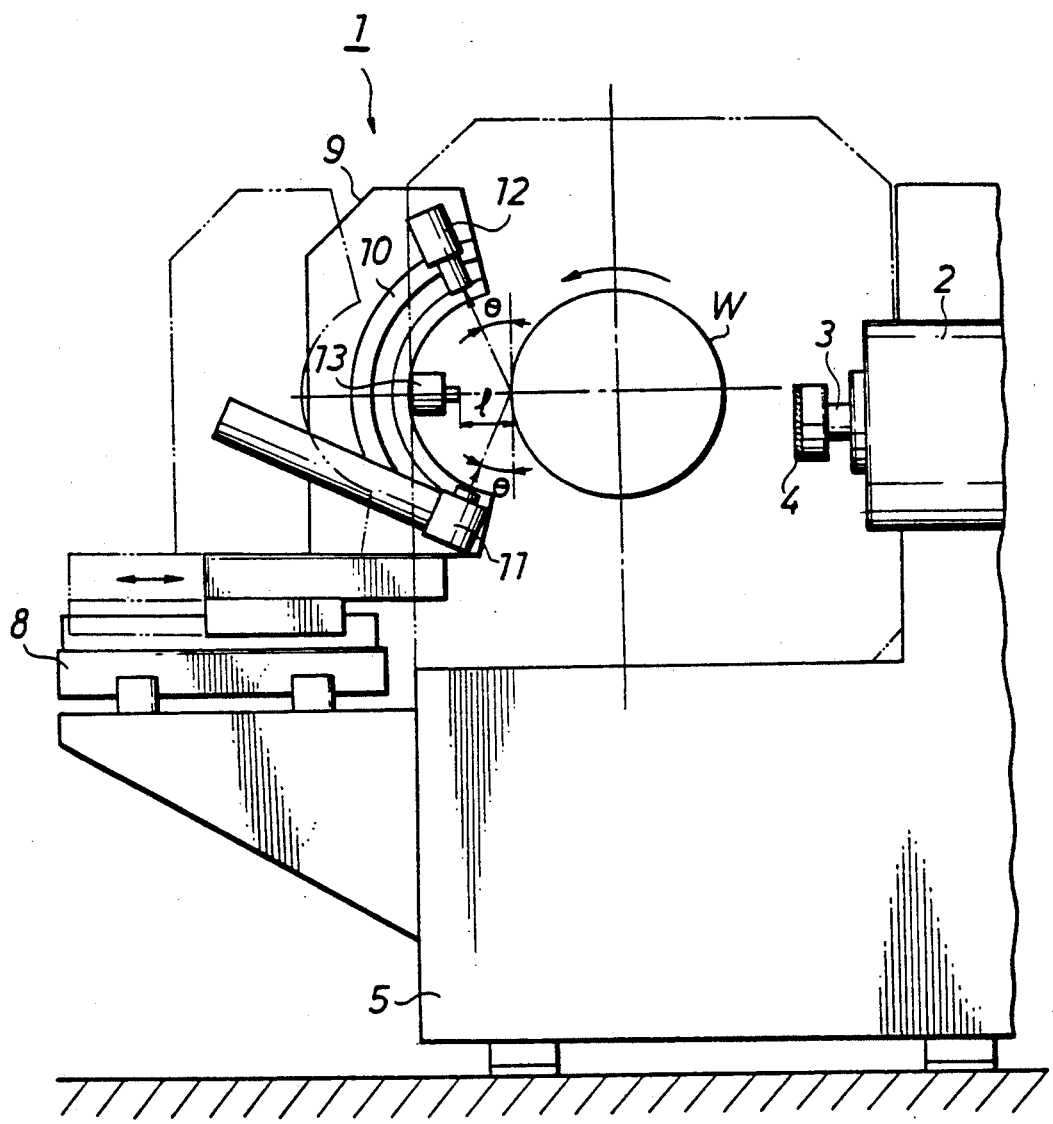
FIG. 2 is a side view of the same apparatus of FIG. 1.
Figure 3:
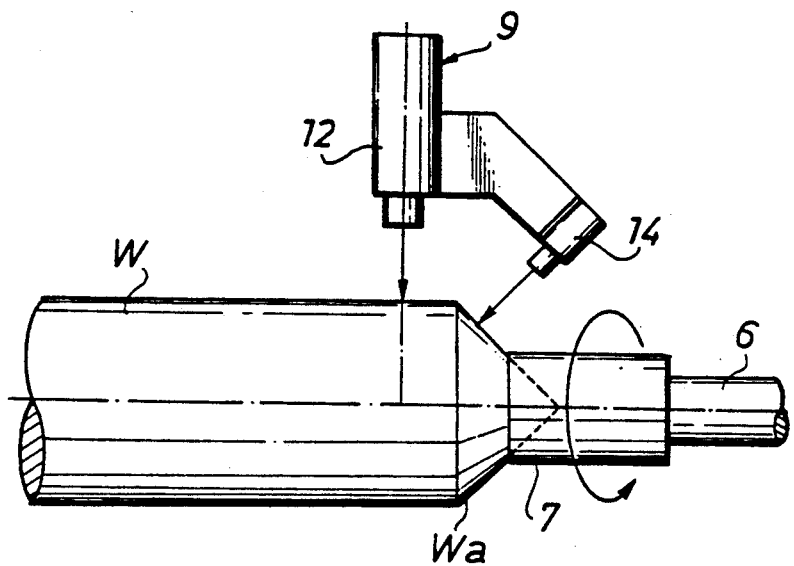
FIG. 3 is a top plan view of a sensor device (consisting of a crystal habit line detector means and an X-ray detector) of the same apparatus of FIG. 1.
Figure 4:
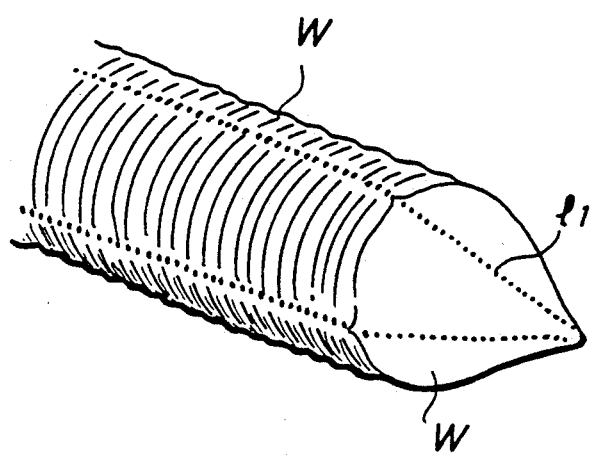
FIG. 4 is a perspective view of a part of a single crystal ingot.

FIG. 1 and FIG. 2 show a crystal orientation detecting apparatus 1; FIG. 3 shows a sensor device 12 (consisting of a crystal habit line detective sensor 14 and an X-ray detector 12); and FIG. 4 shows a single crystal ingot W.

The crystal orientation detecting apparatus 1, according to the invention, is mounted on an external cylindrical grinding machine, and is equipped with a grinder unit 2 which is capable of reciprocating in a horizontal direction indicated by a double-pointed arrow in FIG. 1. A wheel spindle 3 extends horizontally from the grinder unit 2, and carries a grinding wheel 4 at its end.

Incidentally, the wheel spindle 3 is driven to turn by means of a drive means, not shown, incorporated in the grinder unit 2.

Inwardly extending from the end portions of a bed 5 installed on the floor are a pair of horizontal turn shafts 6, 6, which are collinear and carry chucks 7, 7, respectively, at the ends. The turn shafts 6, 6 are adapted to turn, driven by a drive means not shown, in a manner such that their speeds are changed by control and they can be stopped at arbitrary angular positions.

A slide table 8, equipped with an X-ray system 9, is slidably attached to one side of the bed 5. By virtue of the mechanism of the slide table 8, this X-ray system 9 is capable of sliding in the direction parallel to the center line of the single crystal ingot W and in the direction normal thereto, that is, in the directions indicated by the double-pointed arrows X and Y, respectively. The X-ray system 9 is provided with an arcuate goniostage 10, as shown in FIG. 2. An X-ray irradiator 11 and an X-ray detector 12 are engaged with the goniostage 10 in a manner such that they are freely slidable along the arc of the goniostage 10, and can take any arbitrary position on it. Also, as shown in FIG. 2, a position sensor 13 is provided in the X-ray system 9 in a manner such that the center line (the horizontal one-dot chain line in FIG. 2) of the position sensor 13 lies in the same horizontal plane as the center line of the single crystal ingot W does, and that the center line of the position sensor 13 and that of the single crystal ingot W intersect orthogonally with each other. The position sensor 13 is for detecting its distance l from the surface of the single crystal ingot W.

As shown in FIG. 3, a crystal habit line detective sensor 14 is integrally attached to the X-ray detector 12 of the X-ray system 9. This crystal habit line detective sensor 14 is a kind of optical sensor, and adapted to emit a light to the head conical portion Wa of the single crystal ingot W and examine the light reflecting from the head conical portion Wa, to thereby determine whether or not a crystal habit line is being located on the surface of the head conical portion Wa, such as the one designated by 11, as shown in FIG. 4.

Next, the method of the present invention will be more fully explained, as the operation of the crystal orientation detecting apparatus 1 is described with reference to FIGS. 5(a), 5(b), and FIG. 6. Incidentally, FIGS. 5(a), 5(b) is a schematic drawing to show a geometrical relationship between a crystal habit line and the OF, and FIG. 6 is a flow chart showing a procedure of the method according to the invention.

First, a single crystal ingot W, which is pulled up by means of a single crystal pulling apparatus, not shown, is removed from the single crystal pulling apparatus by a robot arm (step 1 of FIG. 6); the ingot W is brought to the crystal orientation detecting apparatus 1 (step 2); the ingot W is clamped between a pair of chucks 7, 7 with the ends chucked by the chucks 7, 7, as shown in FIG. 1 (step 3). Now, the ingot W is held horizontally and adapted to spin about its center line when the turn shafts 6, 6 are driven. Then, the external surface of the ingot W is cylindrically ground by means of the grinder unit 2 (step 4).

The turn shafts 6 are driven by the drive means, not shown, to turn in one direction at a predetermined angular speed, causing the single crystal ingot W to rotate in the same direction at the same angular speed (step 5); meanwhile, the crystal habit line detective sensor 14 determines continually whether or not a crystal habit line 1 is optically detected (step 6). When the crystal habit line detective sensor 14 determines that it detects a crystal habit line 1, the rotation of the single crystal ingot W is stopped (step 7), and it is determined at step 8 which way the single crystal ingot W should be turned during the next step.

Figure 5A:
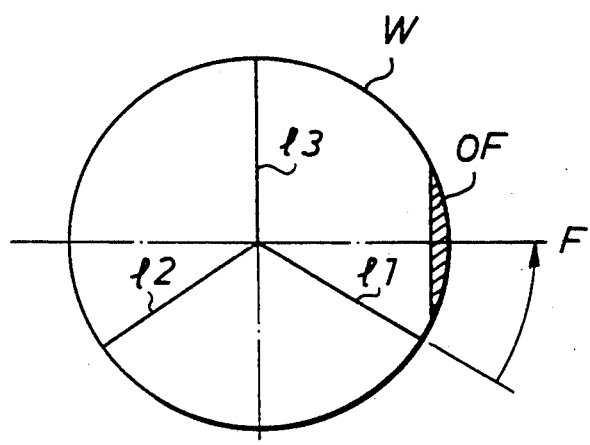
Figure 5B:
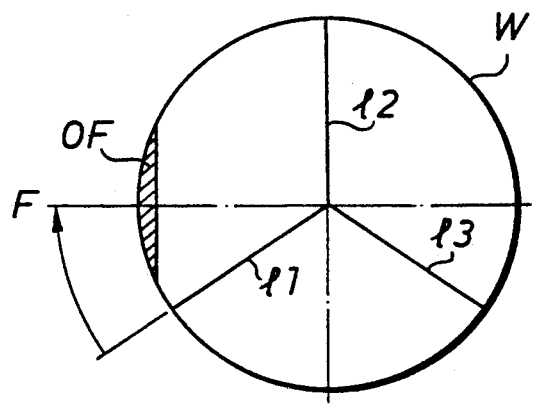
Figure 6:
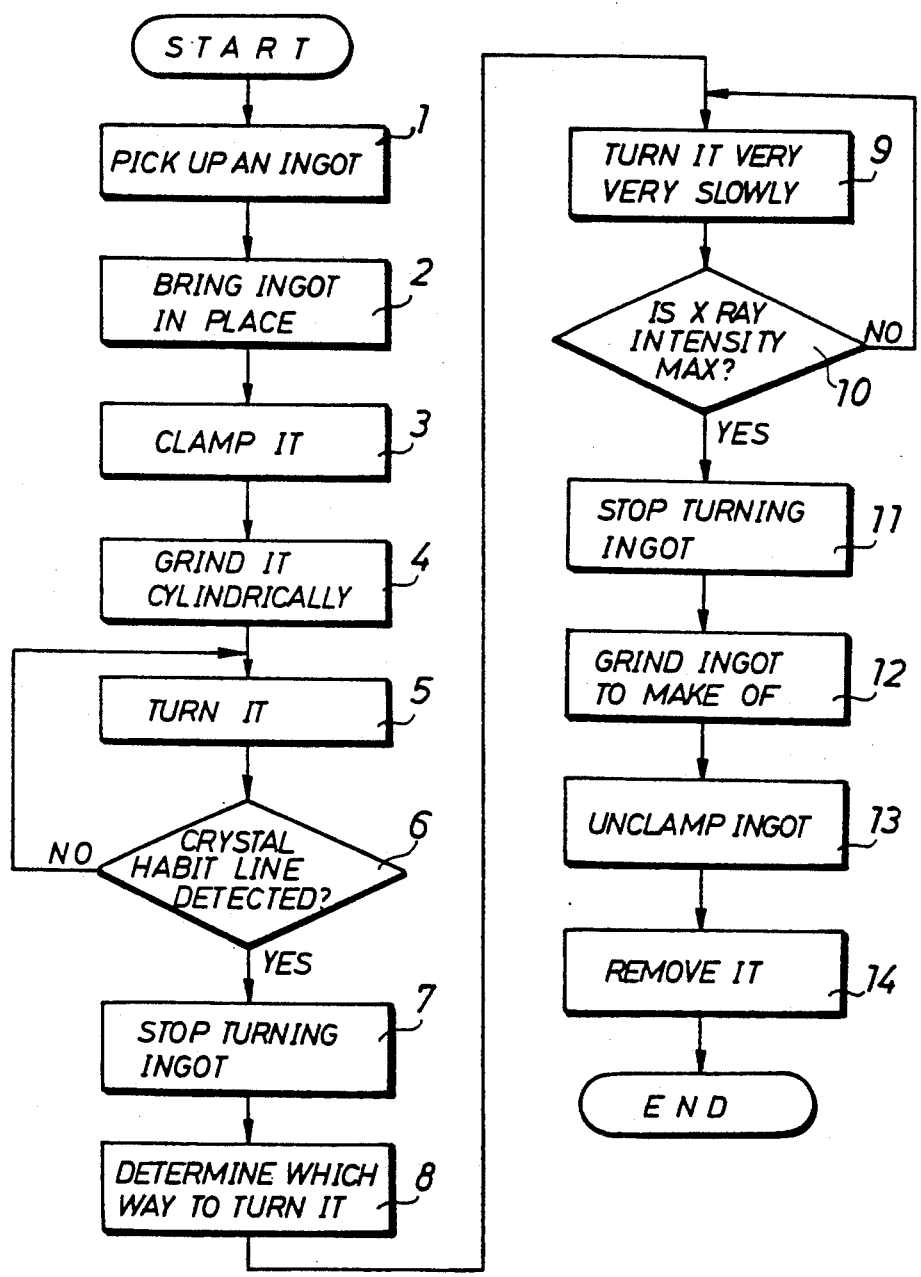
FIG. 6 is a flow chart showing a procedure of the method according to the invention.

Now, with reference to FIG. 5(a), 5(b), the geometrical relationship between a crystal habit line and the crystal orientation will be briefly explained. Generally, in a single crystal, the crystallographic axese hold a fixed geometrical relation with the crystal habit lines: for example, in a <111> crystal, as shown in FIG. 5(a) wherein the head conical portion of the ingot W is seen, a crystallographic axis F lies at an angle of about 30° measured counterclockwise from a crystal habit line 11; or, as shown in FIG. 5(b), a crystallographic axis F lies at a an angle of about 30° measured clockwise from a crystal habit line 11. In FIG. 5(a), 5(b), other crystal habit lines are designated by 12 and 13.

Therefore, after the single crystal ingot W is caused to stop rotating at step 7, the ingot W is again caused to turn in an appropriate direction [counterclockwise in the case of FIG. 5(a), or clockwise in the case of FIG. 5(b)] at a very low angular speed (step 9); meanwhile, the X-ray system 9 is operated to detect the crystallographic axis F. The manner of detecting the axis F is as follows: the X-ray beam is irradiated by the X-ray irradiator 11 onto the surface of the single crystal ingot W at an incident angle of $\theta$ (23.6° in this embodiment), and the beam is reflected by an angle of reflection $\theta$ (equal to the incident angle) from the surface of the ingot W, and the reflected X-rays are detected by the X-ray detector 12. The crystallographic axis F is located by finding out such a point in the ingot surface where the intensity of the reflected X-rays records a maximum value (step 10); when such point is found, the rotation of the single crystal ingot W is stopped (step 11).

At this moment, it is known that the point of the ingot surface at which the X-ray beam is aimed is where the crystallographic axis F passes radially, and the OF should be made orthogonal to this axis F. Thus, the single crystal ingot W is fixed in this position and the grinder unit 2 is operated such that the grinding wheel 4 is turned fast and brought in contact with the single crystal ingot W and grinds off that portion thereof which is hatched in FIG. 5(a), 5(b) as the grinder unit 2 is moved along the length of the single crystal ingot W from one end to the other end thereof (step 12). Thus, a desirous OF, as shown in FIG. 5(a), 5(b), is produced in the single crystal ingot W.

As described above, in the present embodiment, the measurement is required only a small number of times in detecting the crystallographic axis by means of the X-ray system 9, that is, once the approximate location of the crystallographic axis is found in relation to the crystal habit line, the measurement of the X-ray intensity is only to find out where it peaks, so that the measurement operation can be completed in a shorter time and in a simpler and more efficient manner, and the precision in determining the crystallographic axis to provide the guide for OF machining is improved.

Also, according to the invention, the crystal orientation detecting apparatus 1 is only additionally provided with a comparatively inexpensive crystal habit line detective sensor 14 attached to the existing X-ray system 9, so that the apparatus 1 remains as a relatively simple apparatus and inexpensive.

The single crystal ingot thus formed with an OF is unclamped (step 13), and the chucks 7, 7 release the ingot W to be removed from the crystal orientation detecting apparatus 1 (step 14).

Figure 7:
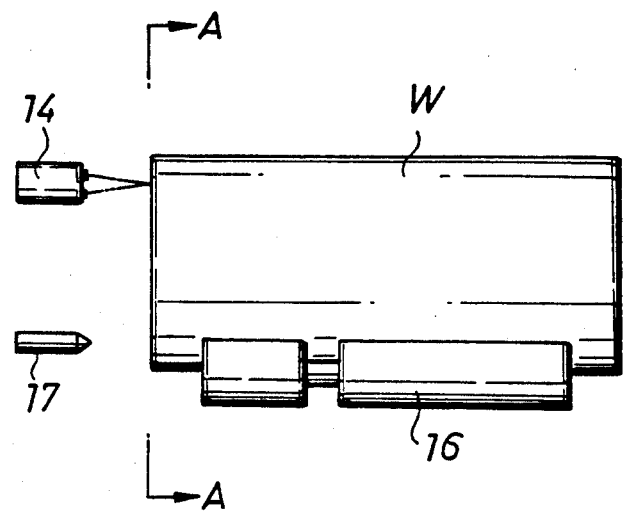
FIG. 7 is a front view of the major elements of another embodiment of the crystal orientation detecting apparatus according to the invention.
Figure 8:
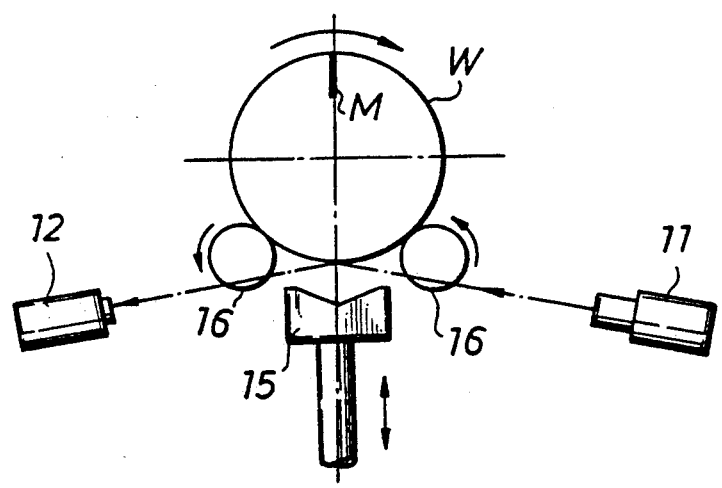
FIG. 8 is a view of the same elements of FIG. 7 as viewed in the direction of arrows A.

Incidentally, in the case where the crystallographic axis is detected of a single crystal ingot W of which the conical portions are already cut off, as shown in FIG. 7 and FIG. 8, the single crystal ingot W is set horizontally on a pair of parallel turn rollers 16, 16, by means of an ingot carrier 15, and as the turn rollers are driven to turn in the same direction at the same speed, the single crystal ingot W is turned about its center line. On one end face of the single crystal ingot W, a crystal habit line detection mark M is put to indicate a crystal habit line, and this mark M is optically detected by the crystal habit line detective sensor 14, which is arranged to face the said end face of the single crystal ingot W. The crystallographic axis is detected by means of the X-ray irradiator 11 and the X-ray detector 12, which are arranged at a lower level than the ingot W. The reference numeral 17 in FIG. 7 designates a marker for marking the position of the crystallographic axis.

RESULTS

As is clear from the above description, a method of detecting a crystallographic axis, according to the invention, makes use of the geometrical relation of the crystallographic axis to the crystal habit lines; and it comprises the following steps: (i) the single crystal ingot is turned about its center line by a turn means capable of changing the angular speed and stopping at an arbitrary angular position, (ii) while the ingot is turned, a crystal habit line is optically detected by means of a crystal habit line detective sensor, (iii) when a crystal habit line is detected, the single crystal ingot is caused to stop turning, (iv) then, the single crystal ingot is turned at a very low angular speed in that direction which will bring a crystallographic axis into the measurement point of the X-ray system sooner, and (v) the X-ray system detects the crystallographic axis; so that the measurement operation has become much simpler, less time-consuming, and more efficient, and as the result, the OF can be made with high precision.

While the invention has been described in its preferred embodiments, it is to be understood that modifications will occur to those skilled in that art without departing from the spirit of the invention. The scope of the invention is therefore to be determined solely by the appended claims.

What is claimed is:

1. A method for detecting a crystallographic axis of a single crystal ingot based on X-ray diffractometry characterized by comprising the steps of: turning the single crystal ingot about its center line at a first speed; optically detecting a crystal habit line; stopping the single crystal ingot from turning when a crystal habit line is detected; determining the rotational direction which will bring a crystallographic axis into the measurement point of the X-ray system sooner; turning the single crystal ingot in the thus determined direction at a second slower speed; and detecting the crystallographic axis by means of the X-ray system.

2. An apparatus for detecting a crystallographic axis of a single crystal ingot based on X-ray diffractometry, comprising; a turn means capable of holding and turning the single crystal ingot about the center line thereof at a a first speed and at a second lower speed selectively, and stopping at an arbitrary angular position; a crystal habit line detector means for optically detecting a crystal habit line of the single crystal ingot; and an X-ray system for detecting a crystallographic axis of the single crystal ingot making use of X-ray diffraction.

* * * * *